United States Patent
Bryan et al.

[11] Patent Number: 6,054,235
[45] Date of Patent: Apr. 25, 2000

[54] COLOR FILTER REPAIR METHOD

[75] Inventors: Michael A. Bryan, Los Gatos, Calif.; C. Wade Sheen, Chester Springs, Pa.

[73] Assignee: Photon Dynamics, Inc., San Jose, Calif.

[21] Appl. No.: 08/925,895

[22] Filed: Sep. 8, 1997

[51] Int. Cl.[7] .......................... G02B 5/20; G02F 1/1335
[52] U.S. Cl. ................................. 430/7; 430/945
[58] Field of Search ............................. 430/7, 321, 945; 349/192

[56] References Cited

U.S. PATENT DOCUMENTS

| | | | |
|---|---|---|---|
| 4,414,566 | 11/1983 | Peyton et al. | 358/101 |
| 4,653,056 | 3/1987 | Baer et al. | 372/27 |
| 4,769,310 | 9/1988 | Gugger et al. | 430/346 |
| 4,894,115 | 1/1990 | Eichelberger et al. | 156/643 |
| 4,925,523 | 5/1990 | Braren et al. | 156/643 |
| 5,079,214 | 1/1992 | Long et al. | 503/227 |
| 5,166,125 | 11/1992 | Harrison et al. | 503/227 |
| 5,260,953 | 11/1993 | Rowe | 372/20 |
| 5,285,750 | 2/1994 | Molian et al. | 119/174 |
| 5,288,528 | 2/1994 | Blanchet-Fincher | 427/596 |
| 5,377,030 | 12/1994 | Suzuki et al. | 359/57 |
| 5,401,616 | 3/1995 | Isumi et al. | 430/258 |
| 5,407,119 | 4/1995 | Churchill et al. | 228/124.5 |
| 5,501,900 | 3/1996 | Harada et al. | 428/323 |
| 5,531,881 | 7/1996 | Matsumura et al. | 204/507 |
| 5,533,447 | 7/1996 | Johnson et al. | 101/211 |
| 5,535,673 | 7/1996 | Bocko et al. | 101/211 |
| 5,581,573 | 12/1996 | Tanuma | 372/72 |
| 5,783,339 | 7/1998 | Watanabe et al. | 430/7 |

FOREIGN PATENT DOCUMENTS

| | | |
|---|---|---|
| 1-096601 | 4/1989 | Japan . |
| 2-092476 | 4/1990 | Japan . |
| 5-027111 | 2/1993 | Japan . |
| 9-005732 | 1/1997 | Japan . |
| 9-108880 | 4/1997 | Japan . |

OTHER PUBLICATIONS

Copending Patent application No. 08/926,769 filed Sep. 8, 1997.

Copending Patent application No. 08/925,609 filed Sep. 8, 1997.

*Primary Examiner*—John A. McPherson
*Attorney, Agent, or Firm*—Townsend and Townsend and Crew LLP

[57] ABSTRACT

A technique including a method 300, 400 and apparatus 200 for repairing a color filter assembly 1 for a flat panel display using a high intensity light source means. The technique provides a color filter assembly having an anomaly. The technique uses a step of directing a high intensity light source 203 through an aperture opening at the anomaly to selectively ablate a portion of the anomaly. These features remove the portion of the anomaly while preventing a possibility of substantial damage to other portions of the color filter assembly surrounding the anomaly.

34 Claims, 7 Drawing Sheets

COLOR FILTER REPAIR METHOD

CROSS-REFERENCE TO RELATED APPLICATIONS

This application is related to application Ser. No. 08/926,769 (Attorney Docket No. 14116-005000), now abandoned, filed on the same date as this present invention and to application Ser. No. 08/925,609 (Attorney Docket No. 14116-005100), now abandoned, filed on the same date as this present application, all in the name of the present assignee. All of these documents are hereby incorporated by reference for all purposes.

BACKGROUND OF THE INVENTION

This present invention relates to techniques for fabricating flat panel displays. More particularly, the invention is illustrated in an example related to the manufacture and repair of a color filter for use in a flat panel display such as an active matrix liquid crystal display (AMLCD) or the like. But it will be recognized that the invention also can be applied to the manufacture of almost any type of color filter media or pixels using a photolithography technique, for example.

The use of a flat panel display such as an active matrix liquid crystal display (AMLCD) or the like continues to grow rapidly. For example, consumer items such as a pocket TV, a notebook computer, an engineering work-station, a high-definition television (HDTV), and others use such a display. Based upon the continued demand for this display, industry has made massive capital investments in creating state-of-art manufacturing lines.

Color flat panel displays are merely an example of a flat panel display, which is being used extensively in computers. These flat panel displays often use color filters to provide the color to the display image. Color filters are generally made using printing-type processes, which are often difficult and costly.

Unfortunately, the color filters are often plagued with defects or anomalies, which are introduced during the manufacturing process. These anomalies include, for instance, inclusions in the color medium and color non-uniformity. Inclusions can be found in the color medium or coating layer. They are often portions of photoresist, particulates, or voids, which define themselves in the color filter. Non-uniform color can be caused by an "overabundance" of color filter material in a pixel. For instance, a red color pixel may have an excessive thickness, which appears to create a deeper or darker display color in relation to surrounding pixels upon illumination. Alternatively, non-uniform color is often caused by a thinner region of color filter material in a pixel. This thinner region appears to lack color or appears "washed out" in relation to surrounding pixels. Furthermore, mask portions may remain on the color filter material where the mask portions block.

A few techniques have been proposed or used to eliminate some of these anomalies. In particular, polishing or grinding tools have been used to remove an overabundance of color filter material from a pixel. These polishing tools generally have a rotatable pad member, which is abrasive. By way of rotation and pressure placed against the color filter material, portions of the overabundant or thicker color filter material are physically removed. These techniques, however, often require great precision to remove a desired amount of color filter material, which often causes a potential for additional damage to the color filter material. Additionally, as pixel sizes decrease, it becomes more difficult to accurately remove color filter material from a pixel.

Anomalies such as portions of photoresist, particulates, or voids generally cannot be removed to repair the color filter. In most cases with enough severity, the color filter plate is rejected and discarded, which is generally expensive and inefficient. As much as 30% of filters manufactured must be discarded due to such defects. Accordingly, the cost of flat panel displays using color filters is often significantly more expensive than other types of displays. In fact, the color filter represents one of the higher cost components of the display. A large portion of these costs is associated with the large number of displays that are rejected due to anomalies, which are introduced into the color filter during the manufacturing process.

From the above, it can be seen that a technique for repairing color filters or removing anomalies from color filters that is easy, cost effective, and reliable is often desirable.

SUMMARY OF THE INVENTION

According to the present invention, a technique including a method and apparatus for repairing color filters or removing anomalies in color filters used in flat panel displays is provided.

In a specific embodiment, the present invention provides a method for repairing a flat panel display and in particular a color filter assembly, having an anomaly, using a high intensity light source means. The color filter includes various elements such as a plurality of color pixels being defined on a transparent substrate, an electrode, and other elements. The method includes a step to direct a high intensity light source through a selected aperture opening at the anomaly to cause an ablation of a portion of the anomaly. This step removes the portion of the anomaly where upon preventing a possibility of substantial damage to portions of the color filter assembly surrounding the anomaly.

In an alternative specific embodiment, the present method provides an apparatus for repairing a flat panel display using a light source means. The apparatus has a high intensity light source, which is used to direct a high intensity light to selected portions of a color filter for ablation purposes. The apparatus also has a selected aperture opening coupled to the high intensity light source. This aperture opening has the selected opening to prevent a possibility of substantial damage to the color filter assembly.

In yet an alternative specific embodiment, the present invention provides a computer program product for repairing a color filter assembly for a flat panel display using a high intensity light source means. The computer program product includes a readable memory having a variety of software codes. The memory includes a first code for directing a high intensity light source through an aperture opening of selected size at an anomaly to a portion of the anomaly to ablate, eliminating the ablated portion of the anomaly. This code directs the light source in a manner where a possibility of substantial damage to the color filter assembly surrounding the anomaly is reduced or minimized. The computer program product can be stored in a variety of memory devices including a hard drive, a floppy drive, a random access memory, and others.

Benefits are achieved by way of the present invention for repairing color filters. These benefits include accurate removal of anomalies, which can repair the color filter to increase overall yields in manufacturing. Additionally, the present invention may employ high powered lasers, without hazardous chemicals or the like. The laser is cost effective and efficient to use. Accordingly, the present invention provides these benefits using a cost effective apparatus and an easy to use technique.

The invention will be better understood by reference to the following detailed description in connection with the accompanying drawings.

DESCRIPTION OF SPECIFIC EMBODIMENTS

Figure 1:
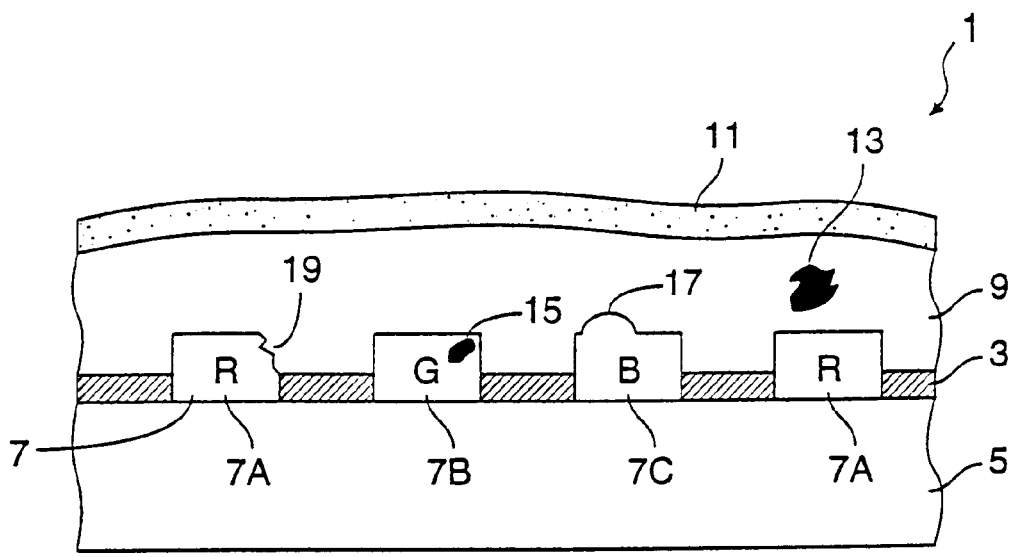
FIG. 1 is a simplified cross-sectional view diagram of a color filter according to the present invention.

As background to the present manufacturing technique, it may assist the reader to understand the numerous types of defects, which may detrimentally influence the quality of the flat panel display. FIG. 1 is a simplified cross-sectional view of one possible AMLCD color filter 1 according to the present invention. This diagram is merely an illustration and should not limit the scope of the claims herein. One of ordinary skill in the art would recognize other types of displays and defects including variations, modifications, and alternatives.

Numerous elements make up the AMLCD color filter 1 including a matrix layer 3, defined on a transparent substrate 5. The matrix layer 3 can be a black matrix or black relief layer defined by printing processes or the like. Transparent substrate 5 is often a clear rigid film or glass-type structure. For instance, the transparent glass structure can be made from materials such as a quartz glass, a borosilicate glass, a soda lime glass, a transparent resin film, an optical resin plate, and other materials. The glass is often transparent and rigid, but can also be flexible in some applications. An example of such a transparent substrate is a glass plate made by Corning, Inc. of New York, which is sold under the product name of Corning 7059 glass. This glass is often used in the manufacture of flat panel displays and the like. The glass plate has a refractive index of about 1.5, and a 1.1 mm to 0.7 mm thickness. Of course, the plate can be made of almost any relatively transparent structure or medium with a refractive index greater than one, relative to its surroundings. The thickness of the plate depends upon the application.

A colored layer 7 is formed in the matrix layer 3 and overlies the substrate. The colored layer generally has a red pattern 7A, a green pattern 7B, and a blue pattern 7C, which can be arranged in a mosaic arrangement, a triangular arrangement, a stripe arrangement, and others. Each pattern includes a plurality of red, green, or blue pixels or the like. Of course, the type of arrangement depends upon the application.

A protection layer 9 is defined overlying the structure including the colored layer 7 and the matrix layer 3. The protection layer 9 is often a dielectric layer such as a silicon dioxide, a silicon nitride, a borosilicate glass, and other materials. Additionally, a combination of layers can be used as the protection layer. For instance, the protection layer 9 can include a silicon dioxide having an overlying layer of silicon nitride or the like.

Electrode layer 11 overlies the protection layer 9. Electrode layer 11 is often made using an indium tin oxide (ITO), but it can also be made of other materials. Other types of color filters can also be repaired by way of the present techniques. An example of one of these color filters used in a display is described in U.S. Pat. No. 5,501,900, assigned to Dai Nippon Printing Co., of Japan, which is hereby incorporated by reference for all purposes.

These color filters often contain a variety of anomalies generally classified as either inclusions or non-uniform color. These anomalies or defects can detrimentally influence display performance. An inclusion may be a void 13 or a particulate contamination 15 found in the color filter assembly, as illustrated by in FIG. 1.

Inclusions can be found throughout the color filter and more particularly in the protection or layer 9 or colored layer 7. Examples of these inclusions include residual resist (or photoresist) material, particles, and the like. These inclusions generally become a problem when they are as large or larger than the cell gap, which effectively blocks the cell. Inclusions can also be voids or separations. These voids or separations become a problem when they become as large or larger than the cell gap.

Non-uniform color can be defined as brightness non-uniformities in the color. These brightness non-uniformities tend to cause pixels that are either darker or lighter than surrounding pixels. Non-uniform color is often caused by a non-uniform film of color filter material or the like in the color pixel region. In most cases, the non-uniform color is a "bump" 17 in the color pixel, which is predominately color filter material. Alternatively, the non-uniform color is a "depression" 19 in the color pixel, which is caused by a recessed region in the color pixel. As one may suspect, the "bump" generally causes an appearance of a darker or deeper coloring, when viewing the flat panel display by way of illumination. Alternatively, the "depression" causes an appearance of a lighter region of color in the pixel. Depending upon the intensity of light illuminating from the "depression", or "bump", or spike, " the color filter may be categorized as a reject.

The above anomalies may also exist in other regions of the color filter assembly. For instance, they may be present in the matrix layer 3, the transparent substrate 5, the electrode layer 11, and others. Depending upon the location and the nature of the anomaly, it may be removed or substantially reduced in size by way of the present invention. Details of the present invention including an apparatus and method are shown by way of the figures below.

Figure 2A:
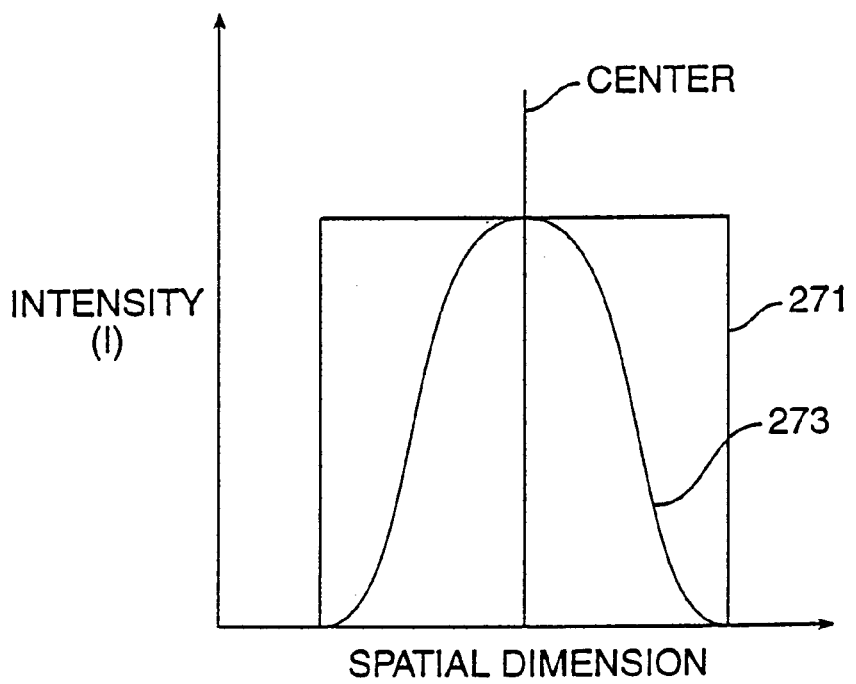
FIG. 2A is a simplified diagram of a laser beam profile according to the present invention.
Figure 2:
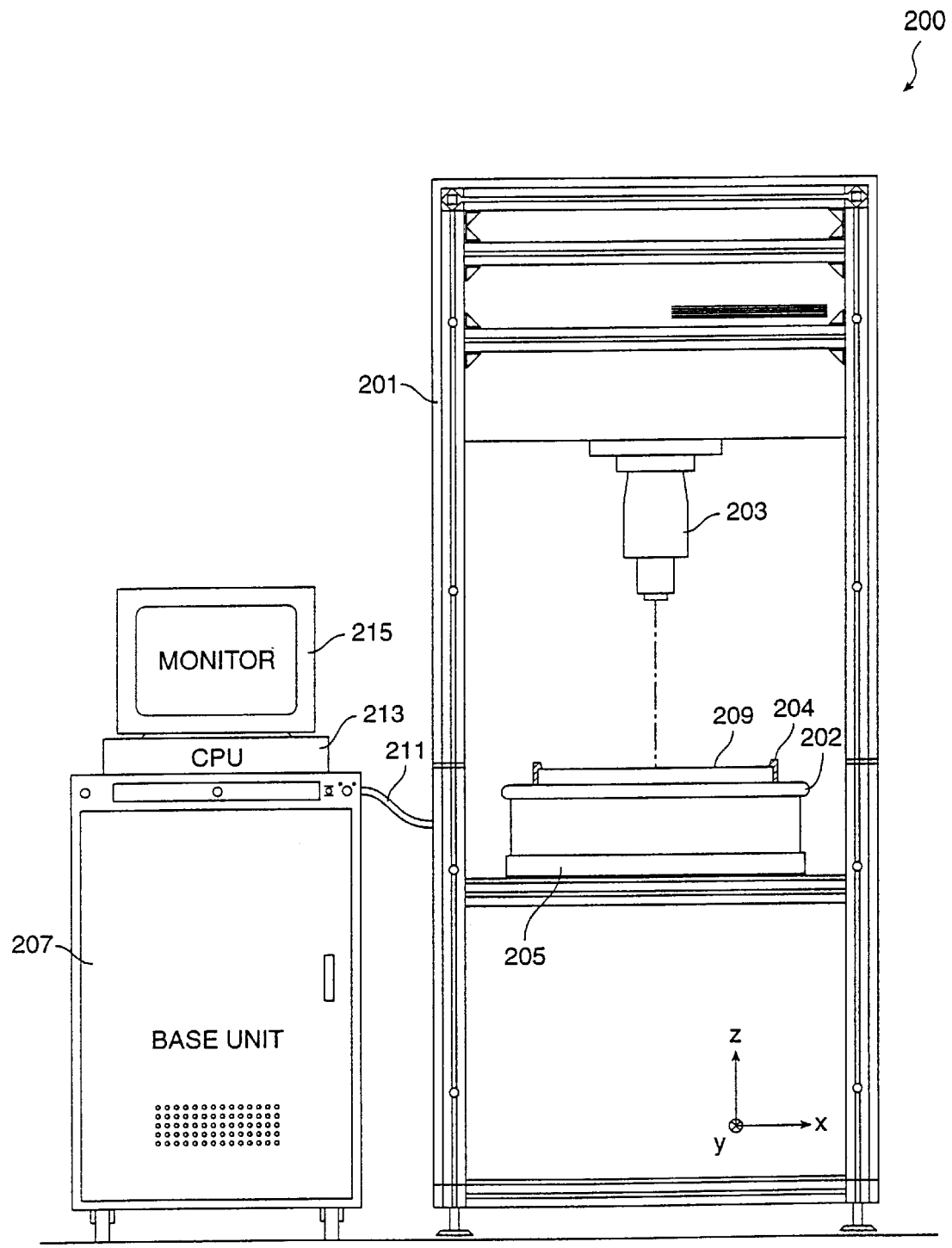
FIG. 2 is a simplified diagram of a cutting tool used to repair the color filter of the above Fig. according to the present invention.

In a specific embodiment, a cutting tool system 200 is used to direct a high intensity light source towards the anomaly for ablation purposes, as illustrated by FIG. 2. This diagram is merely an illustration and should not limit the scope of the claims. The cutting tool system 200 includes a housing 201, a laser apparatus 203, an x-y-z stage assembly 205, a base unit 207, and other elements.

The housing 201 encloses the laser apparatus 203, which is positioned over the x-y-z stage 205. The x-y-z stage 205 holds a color filter assembly 209, which is positioned for repair. The color filter assembly positions on a slidable table 202, and a hinged frame 204, which is brought down to secure the color filter assembly in place. The slidable table 202 allows for easy positioning of the filter in an x-y plane under the laser apparatus 203.

The slidable table allows the filter to be shifted in the x-y directions relative to the laser apparatus. The x-y stage can be any suitable unit capable of moving the filter in an x-direction and/or a y-direction. The stage may include continuous movement in the x-direction and/or y-direction. Preferably, the x-y stage also increments at selected dimensions in the x-direction and the y-direction. Stage movement occurs by way of actuators, drive motors, and the like. The stage accuracy is 1 micron and less or 0.5 micron and less. Alternatively, the laser apparatus is mounted onto an x-y stage to move the laser apparatus relative to the filter. Alternatively, multiple laser apparatuses can be used to repair different regions of the color filter assembly.

In a preferred embodiment, the x-y-z stage assembly is a hybrid mechanical and air bearing stage with a linear servo such as a product made by Dover or Anorad. This stage has a maximum speed of 320 mm/s, a step speed of 30 mm in 300 ms, an accuracy of 5 $\mu$m, a resolution of 5 $\mu$m, and a travel of 720 mm×720 mm. This stage provides for fast and accurate movement between anomalies. In this embodiment the stage is large enough to accommodate an array for repair.

The z-direction also operates in a continuous movement mode or at selected z-positions through the use of an actuator (drive motor or the like). The actuator can be in a two-stage or multi-stage actuator. The z-direction may also operate in a stepping mode. Of course, exact incremental dimensions in the x-direction, the y-direction, and the z-direction depend upon the particular application. In other embodiments, the stage has movement in the z-direction, but does not adjust in the x-y direction during inspection. Stage accuracy in the z-direction is 2 micron and less or 1 micron and less. In further embodiments, the laser is adjustable in the z-direction relative to the filter.

The laser apparatus can be any suitable design capable of ablating portions of the color filter assembly. These portions of the color filter assembly include anomalies and the assembly itself. This laser apparatus has a sufficiently rich energy source to remove or ablate portions of the filter assembly, which remove or substantially reduce in size anomalies. These anomalies can be inorganic materials such as certain types of particulate contamination in the protective layer. Alternatively, anomalies can be made of organic material such as photoresist or a portion of the color filter material or the like. In most cases, the laser apparatus ablates portions of the color filter in a few seconds or less (e.g., milliseconds to microseconds and less), which does not substantially damage the color filter assembly.

In most embodiments, however, the laser should have sufficient strength to expose the color filter material by ablating the protective layer, which is generally made of an inorganic material, e.g., silicon dioxide, silicon nitride, etc. Suitable lasers can have energy sources that radiate energy at a wavelength in the UV range, in the visible range, and/or infra-red range. Preferably, the wavelength is the 180 to 11,000 nm range and is often at about 550 nm or less.

Examples of these energy sources are solid state pulsed lasers such as ruby lasers or frequency multiplied Nd:YAG lasers, pulsed lasers with boosters such as pulsed dye lasers or a Raman Shifter, and also continuous wave lasers with pulsed modifications. Other lasers that can be employed include CW ion lasers (Ar, Kr), as well as pulsed metal vapor lasers, for example, copper vapor lasers or gold vapor lasers, or high capacity pulsed semiconductor lasers, and also pulsed gas lasers such as excimers and the like.

Other characteristics of the laser apparatus would include adjustable parameters to accompany the material to be removed or ablated. For instance, the laser apparatus has adjustable pulse content, pulse shape, and pulse duration. Additionally, the laser has an adjustable aperture to increase or reduce the size of the selected target area or region. These parameters are adjusted to selectively remove the desired material from the color filter assembly or the like.

In a preferred embodiment, the laser apparatus includes the following characteristics. The laser apparatus is an Nd:YAG source having a wavelength of about 1.06 $\mu$m and less. The laser generally operations in this UV wavelength range, but can also be operated in the IR and visible wavelength ranges. The beam cross-section profile shape is generally "top hat" 271 in nature, rather than conventional Gaussian profile(s) 273 in common lasers, as shown in FIG. 2A, for example. Additional features of the laser apparatus include optics and apertures for beam focussing and aperture control, among others. The laser also has a finely controlled aperture with beam spot, ranging from about 1 $\mu$m to about 50 $\mu$m in both x and y directions, which provides a resolution of 0.2 micron and less. Additional features of the laser include, but are not limited to, a 40 mW average power, a 15 ns pulse time, a 30 mJ fundamental pulse energy, a 20 pulse/sec pulse rate, a flash lamp pump source, a 10 million pulse lifetime, and an attenuator capable of 0% to 95% attenuation. Of course, other parameters could be used depending upon the application.

The cutting tool 200 is controlled via base unit 207, which is coupled to the cutting tool through the housing using lines 211. The base unit can be any suitable control unit for controlling the movement of the laser apparatus and/or x-y-z stage for positioning purposes. The base unit also controls the intensity and duration of the laser pulse, which is directed at the anomaly. Other features of the base unit would include easy programmability, sufficient memory, and network capability. The base unit 207 generally includes a central processing unit 213, a keyboard and mouse interface, a color display 215, and other elements. In a preferred embodiment, the base unit includes a SPARC 5 station manufactured by Sun Microsystems, Inc. This embodiment includes a 170 MHz clock speed, a 1.2 GB hard disk drive, a 1.44 MB floppy disk drive, a 64 MB RAM, and either a 20" monitor. The base unit includes sufficient memory, which can store a variety of process recipes, such as those described below and others.

The present cutting tool provides an apparatus which can be used to remove or substantially eliminate portions of anomalies in the color filter assembly. This cutting tool is generally a laser apparatus such as the one described above, which directs a high intensity light source at an anomaly for ablation purposes. The laser apparatus can selectively remove anomalies from the color filter assembly in an easy and cost efficient manner. This apparatus provides for the repair of the color filter assembly used for the manufacture of flat panel displays and the like.

In a specific embodiment, the invention provides a technique for ablating anomalies from a color filter. This ablating technique generally sears, burns, or vaporizes the anomaly. In most embodiments, the anomalies include particulate, portions of photoresist, pattern defects, and the like, which were described above. The technique for ablating anomalies can be briefly described as follows:

1. Provide a color filter having an anomaly;
2. Direct an aperture opening of a cutting device (i.e., laser tool, etc.) toward the anomaly;

3. Set the aperture of the cutting device to encompass the anomaly;
4. Direct a high intensity light source through the aperture to ablate the anomaly;
5. Repeat steps (3) and (4) until the anomaly is substantially removed, if necessary;
6. Perform remaining fabrication steps.

Figure 3:
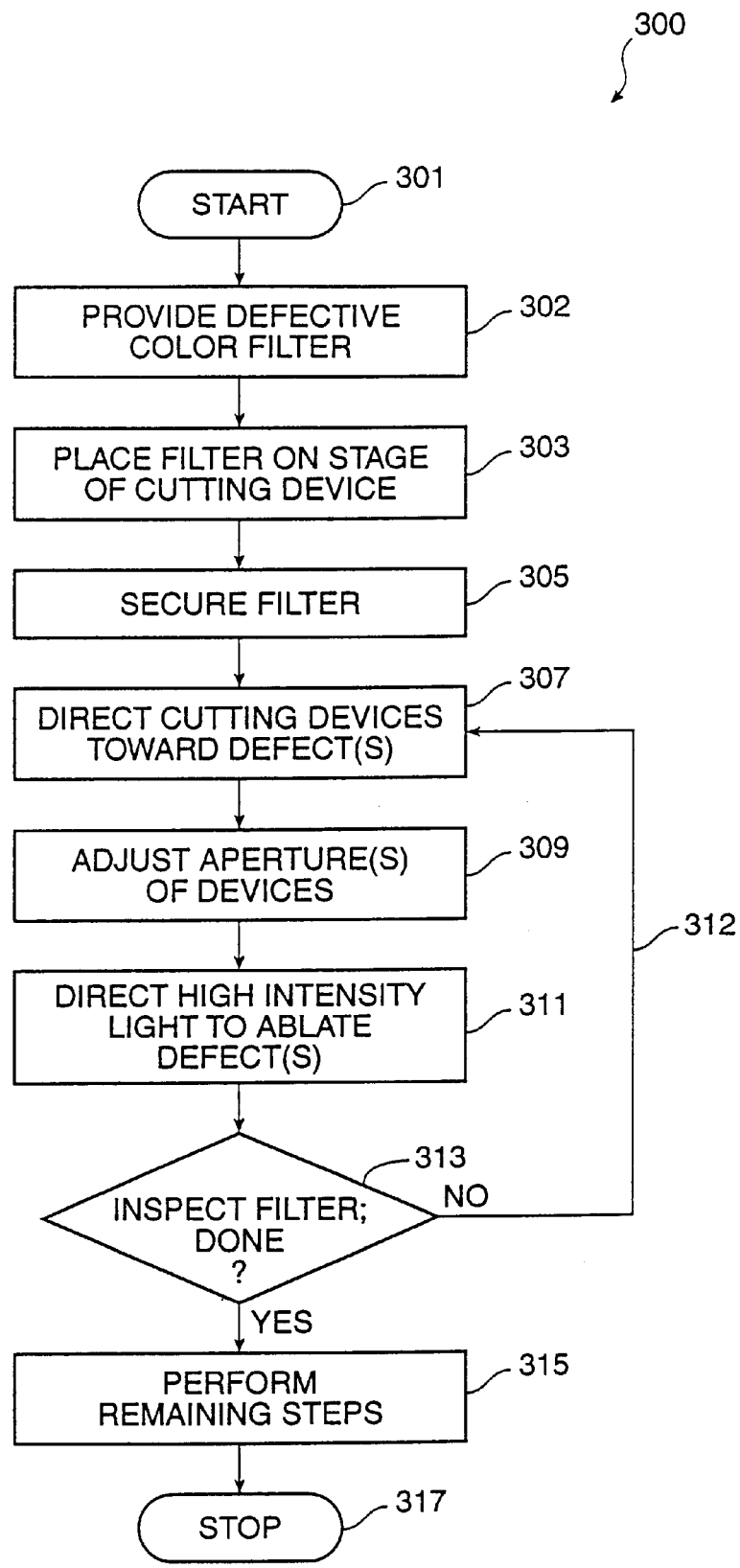
FIG. 3 is a simplified flow diagram for removing anomalies from the color filter of the above Fig. according to the present invention.

As shown, this technique generally directs the cutting device toward the anomaly and directs a high energy light source (i.e., laser) to ablate the anomaly. If needed, the aperture of the cutting device is reset and the high energy light source is directed to remaining portions of the anomaly for removal. These sequences of steps can be repeated, as necessary. Details of these steps are shown by way of the simplified flow diagram of FIG. 3. FIG. 3 is a simplified flow diagram 300 of a technique for removing anomalies from a color filter according to the present invention. This flow diagram 300 is merely an illustration and should not limit the scope of the claims herein.

The flow diagram begins at step 301. The flow diagram illustrates a method for repairing a color filter assembly. The method includes a step of providing a defective color filter assembly 302. This defective color filter assembly includes anomalies, which can be defined as inclusions or color non-uniformities. Details of these anomalies were previously described.

The color filter assembly is placed on a stage (step 303) of a cutting tool, such as the one described by way of FIG. 2. The color filter is firmly placed on a stage assembly, which allows for accurate positioning of a high intensity light source onto a selected portion of the filter assembly. In preferred embodiments, the color filter assembly is secured (step 305) using a cover to prevent any substantial movement of the assembly during processing.

The cutting tool and in particular a laser apparatus is directed (step 307) toward a defect, i.e., anomaly. This directing step is performed by moving the x-y-z stage such that the anomaly is directly underneath an aperture of the laser apparatus. Alternatively, the laser apparatus is moved via a stage relative to the filter assembly, which is fixed in location. As a further alternative, the laser may be pivoted to aim at the desired anomaly with or without moving the stage or the laser horizontally.

The aperture (step 309) is adjusted to provide a selected amount of light intensity onto a selected region of the color filter to ablate the anomaly. In one embodiment, the aperture is opened to point where the light directed through the aperture encompasses the entire anomaly. This allows a top portion of the anomaly to be ablated or removed.

If needed, an intermediate step (not shown) of directing energy through the aperture may be performed to remove a portion of the electrode layer 11 between the cutting devices and the anomaly. This intermediate step removes the portion of the electrode layer that may otherwise prevent ablation of an underlying anomaly.

A step of directing a high intensity light source at the anomaly is performed (step 311). This step can remove a portion or a substantial portion of the anomaly. In most embodiments, an upper portion of the color filter assembly is also removed by way of the high intensity light source, if the anomaly is disposed in a center portion of the protective layer or the color filter material or the like. The light source is preferably directed to the anomaly in a perpendicular direction to the surface of the color filter.

The intermediate step may require more energy than that required to ablate an anomaly. Thus, the laser may produce a high-energy beam during the intermediate step, but may then be reduced in energy or even shut off during step 311.

The intermediate step may require a different wavelength of energy than step 311. In this case, the laser may produce a wavelength of light needed to remove the electrode layer during the intermediate step and another wavelength of light needed to ablate an anomaly during step 311. Alternatively, the laser may produce both wavelengths of light simultaneously.

After ablating a portion of the anomaly, the color filter assembly is inspected (step 313). Inspection can occur using simple visual inspection techniques under magnification, e.g., microscope, magnifying glass, etc. Alternatively, inspection can occur by observing the ablated region using a high quality CCD camera or the like. Or course, the type of inspection used depends upon the particular application.

If the anomaly has not been removed adequately, the method returns to step 307 via branch 312. Here, the laser apparatus is re-directed to the anomaly, the aperture is readjusted to allow a selected amount of light intensity through the aperture, and a high intensity light source is directed through the aperture to ablate a remaining portion of the anomaly. The method reinspects the ablated anomaly. Alternatively, reinspection is not necessary when the anomaly is removed. If the anomaly has been adequately removed, the color filter assembly is returned to the manufacturing process and additional process steps are performed. Alternatively, if the anomaly has been removed adequately, the color filter assembly returns to the remaining process steps (step 315). These remaining process steps include cleaning or reinspection and others. A final inspection step may also be used in the present method. The method ends at step 317. Of course, this depends upon the particular application.

The above sequence of steps is merely an example. These steps can be further combined or even separated into additional steps. Steps can even be inserted, depending upon the application. These and other steps are performed by way of the present invention.

In an alternative embodiment, the invention provides a technique for reducing the size of bumps on a color filter pixel. This technique may be briefly outlined as follows:

1. Provide a color filter having an anomaly (e.g, bump, etc.);
2. Positioning a cutting device to direct the cutting device toward the anomaly;
3. Set an aperture opening of the cutting device to encompass an outer periphery of the anomaly;
4. Direct a high intensity light source through the aperture to ablate a portion of the anomaly;
5. Reduce the aperture opening of the cutting device to encompass an inner periphery of the anomaly;
6. Direct a high intensity light source through the reduced aperture to ablate an inner periphery of the anomaly;
7. Repeat steps (5) and (6) until the anomaly is substantially removed;
8. Perform remaining fabrication steps.

The above sequence of steps selectively reduces the size of the anomaly by way of each step of directing the high intensity light source to ablate a portion of the anomaly. These steps "surgically" remove or eliminate the anomaly from the color filter in an accurate and easy manner. In particular, adjusting the aperture opening of the cutting device to selectively remove portions of the bump in multiple steps removes the bump without causing severe damage to the color filter assembly. Details of the technique are shown in the Figs. described below.

Figure 4:
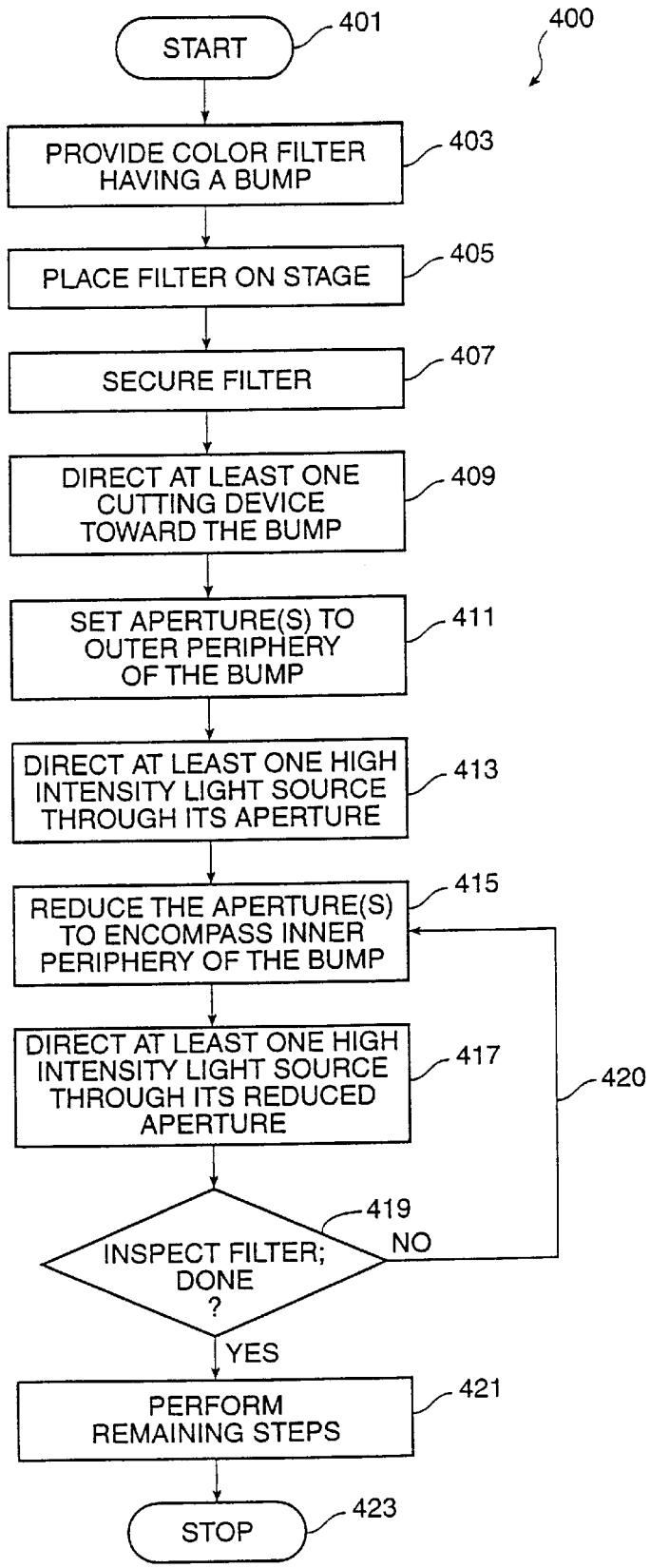
FIG. 4 is a simplified flow diagram for removing protrusions or "bumps" from the color filter of the above Fig. according to the present invention.

FIG. 4 is a simplified flow diagram 400 for a technique in removing bumps from the AMLCD color filter of the above Fig. This diagram is merely an illustration and should not limit the scope of the claims herein. One of ordinary skill in the art would recognize other variations, modifications, and alternatives. The technique for removing bumps is also illustrated by way of FIGS. 5–7.

The flow diagram begins at step 401. A color filter assembly (step 403) is provided. The color filter assembly is similar to the one described above, but can also be others. The color filter assembly has a plurality of pixel elements (e.g., red, green, and blue). One of these pixel elements includes an anomaly such as the one shown in FIG. 5. The anomaly can be categorized as a "bump" 501 or protrusion, which increases the intensity of the color at this region. The increased intensity of color appears to look like a deeper or darker color than surrounding regions.

The color filter assembly is placed on a stage (step 405) of a cutting tool, such as the one described by way of FIG. 2. The color filter is firmly placed on an assembly stage, which allows for accurate positioning of the high intensity light source onto the filter assembly. In preferred embodiments, the color filter assembly is secured (step 407) using a cover to prevent any substantial movement of the assembly during processing.

Figure 5:
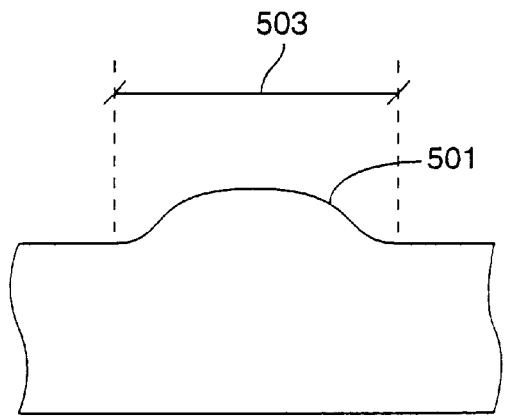
FIGS. 5–7 illustrates cross-sectional view diagrams of a color filter according to the present invention.
Figure 6:
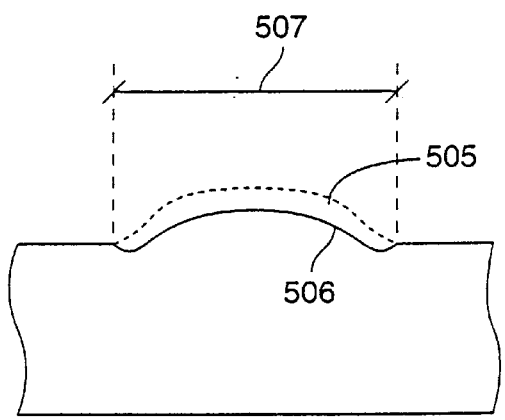

The aperture of the laser is adjusted to target the bump in step 411. This aperture is adjusted to allow the laser to target a region 503 of the entire bump, which begins at an outer most periphery of the bump, as illustrated by FIG. 5. The aperture is adjusted to selectively remove an upper layer of the bump over the entire upper surface of the bump.

A step of directing the high intensity light source is provided in step 413. The high intensity light (or particle source) can be from a laser such as the one previously described. Alternatively, other lasers or light sources can be used, depending upon the application. As can be seen from FIG. 6, the high intensity light source removes an upper layer portion 505 of the bump over the entire upper surface region. The bump 506 is now reduced in size, e.g., height and width.

The aperture is reduced to target an inner portion 507 of the original bump (step 415). The technique selects a reduced aperture size to remove another portion of the bump. High intensity light is directed (step 417) onto the reduced target area to remove a second portion of an upper layer of the bump, which further reduces the bump size including the width and height.

Figure 7:
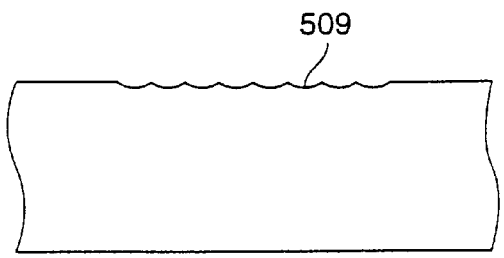

The ablated structure is inspected (step 419). If additional ablation is needed, steps 415 and 417 are repeated until the bump has been substantially removed via branch 420. The ablated structure which has been repaired is shown in FIG. 7. As shown, the ablated color filter assembly does not have a "bump." The ablated structure includes upper surface region 509, which is substantially free from damage.

Remaining fabrication steps are then performed on the color filter (step 421). These steps can include coating the ablated structure using a clear film of protective layer. The coating layer tends to protect the underlying filter layer. The coating layer can be selected from polymers or oxides (e.g., ITO, $SiO_2$) and others. A variety of additional processing steps also can be performed, depending upon the application.

The technique for removing bumps can also be applied to removing large inclusions found near a surface region of the color filter assembly. Alternatively, the technique can also be applied to anomalies within the color filter assembly. That is, the anomalies can be in the protective layer, in the electrode layer, in the matrix layer, or the substrate. Accordingly, above techniques can be used to remove a variety of anomalies to repair a color filter or the like.

Also, as an alternative to the above description, the aperture may be set to encompass an inner periphery of the anomaly at step 411 and increased to encompass a larger periphery, and eventually an outer periphery, of the anomaly at step 415.

Although the invention has been described in terms of selected sequences of steps, the invention can be varied or modified, depending upon the application. For example, the invention can be combined or even separated using a variety of hardware and software features. For example, the hardware can be in the form of a microprocessor based unit with software. The software can include a variety of recipes to carry out the above techniques as well as others. The software can be described as a computer program product (e.g., software, firmware), which is stored in memory, but can also be stored on a transferable medium such as a floppy disk, a CD ROM, a removable hard drive, a tape, and others.

Experimental Section

To prove the principle and operation of the present invention, experiments were performed. These experiments were merely shown as an example of the usefulness of the technique as applied to color filters according to the present invention. The technique can also be applied to a variety of other applications.

In these experiments, commercial lasers and color filters were used. In particular, the laser was a YAG laser manufactured by New Wave. The laser emitted high intensity light from IR, VISIBLE, to UV wavelengths. These wavelengths seem to provide ablating characteristics.

The aperture of the laser was also adjustable to ablate selected regions of the color filter assembly. The aperture was set to remove a portion as large as a pixel or multiple pixels. The aperture could also be set to remove a portion as small as 1 $\mu$m. The aperture was adjustable so that the portion being treated by the laser could be increased or decreased accurately by dimensions of 0.5 $\mu$m.

The color filter assembly was a commercial unit manufactured by DAI Nippon Printing or Tappan Printing. This color filter is believed to be similar to those manufactured by all manufacturers. This filter, however, had a defective region, which had an anomaly in the form of a bump, which is often color filter material or a "spike" of ITO material. Upon inspection, the bump or spike appeared as a deeper or darker color region than surrounding regions of the color filter. The color filter was believed to be a typical commercial color filter having bump thereon.

In this experiment, high intensity light from the laser selectively ablated portions of the bump using successive cuts to remove a substantial portion of the bump. The aperture opening was set to ablate a region having a dimension of 10 $\mu$m by 10 $\mu$m. The aperture opening was re-set at increments of 2 $\mu$m. High intensity light was directed through the aperture opening to make successive cuts or ablations on the bump or spike. By way of the ablating technique, the color filter was repaired. Photographs of the color filter were made before and after the ablating technique.

Figure 8:
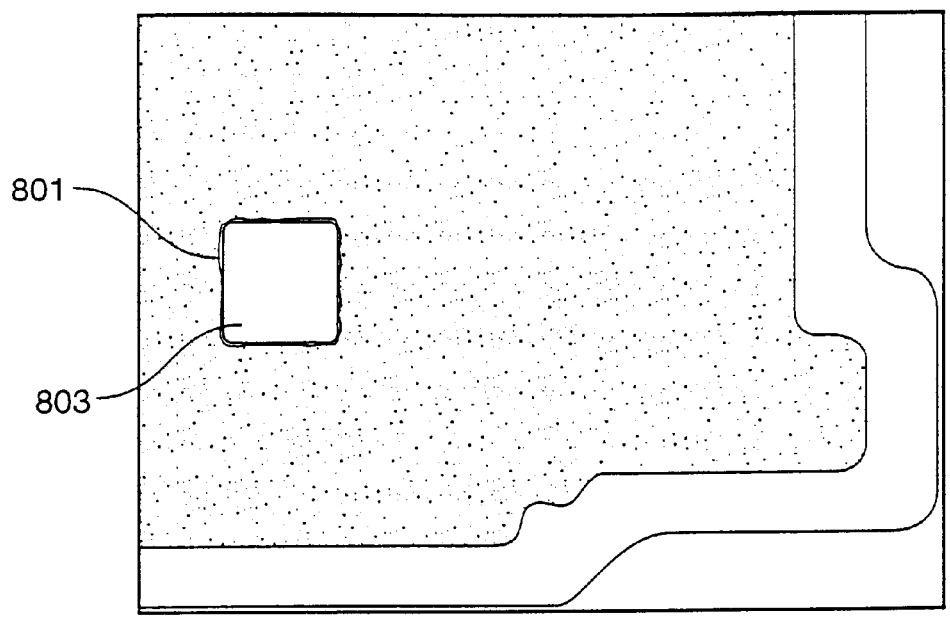
FIGS. 8–10 are photographs of a color filter according to the present invention.
Figure 9:
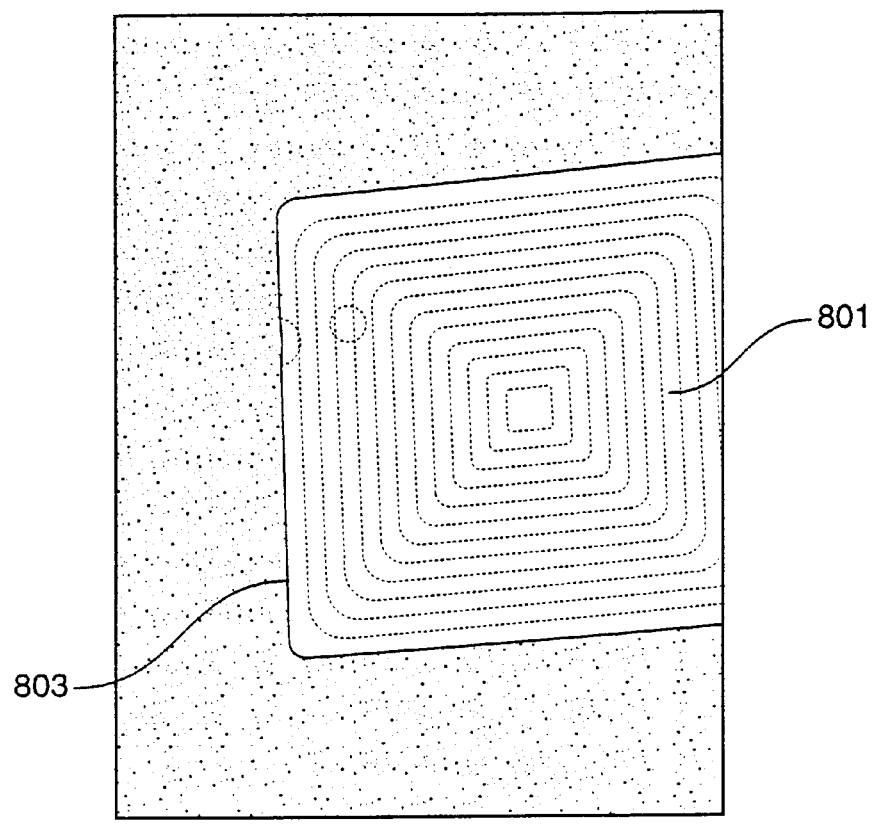
Figure 10:
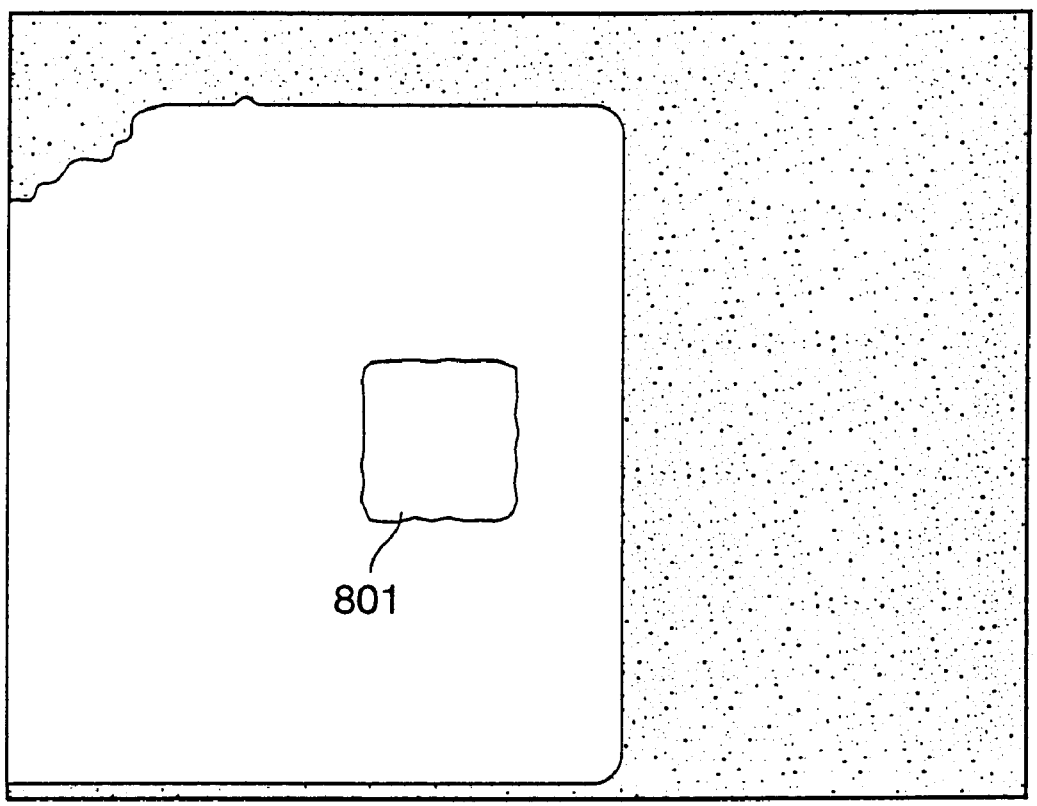

FIGS. 8–10 are photographs of the color filter assembly during selected steps of the ablating technique. The color filter before ablating includes a portion which has a bump or spike. The bump or spike appears to have a deeper or darker color than surrounding regions. After a substantial portion of the bump was ablated using the present technique, photographs were taken. As shown in FIGS. 8 and 9, the present ablating technique removed a substantial portion of the bump, which is shown in the square region 801. This photograph was taken using conventional illumination, i.e., white light. As shown, the ablated portion appears to have a definite outline region 803, which was first believed to be damaging than the color filter.

The filter, however, when exposed to light in a transluminous mode appears quite different than conventional illumination. As can be seen in the photograph of FIG. 10, the outline region caused by the ablating process is substantially invisible to the naked eye. In this photograph, which was taken using a 500× microscope, the outline region was almost invisible.

Accordingly, the present ablating technique was successful in removing the bump without damaging the color filter assembly. In fact, it was difficult to believe that in transluminous mode the outline region would substantially disappear. These results were unexpected.

The invention has now been explained with reference to specific embodiments. Other embodiments will be apparent to those of ordinary skill in the art in light of the disclosure. For example, high intensity energy sources have been described as light sources. Energy sources for energy waveforms having wavelengths other than those for visible light may be used. It is therefore not intended that this invention be limited, except as indicated by the appended claims.

What is claimed is:

1. A method for repairing a color filter assembly for a flat panel display using a high intensity light source means, said color filter assembly having an anomaly, said color filter assembly having a plurality of color pixels being defined on a transparent substrate, said method comprising steps of:

directing a high intensity light source through an aperture opening of selected size at said anomaly to a portion of said anomaly to ablate, eliminating said ablated portion of said anomaly; and successively directing the high intensity light source at said anomaly using successively diminishing aperture size.

2. The method of claim 1 wherein said anomaly is selected from a group consisting of a particle, a photoresist, a pattern defect, a bump, a spike, or a bubble.

3. The method of claim 1 wherein said anomaly is defined in a portion of said filter selected from a group consisting of a protective layer, a matrix layer, and an electrode layer.

4. The method of claim 1 wherein said anomaly is defined in at least one of said pixels.

5. The method of claim 1 wherein said anomaly has a dimension of 10 microns and less.

6. The method of claim 1 wherein said directing step has a positioning accuracy of 1 micron and less.

7. The method of claim 1 wherein said directing step has a positioning accuracy of ½ micron and less.

8. The method of claim 1 wherein said directing step is provided in about 2 seconds and less.

9. The method of claim 1 wherein said high intensity light source is substantially at a wavelength of about 180 nm to about 11,000 nm.

10. The method of claim 1 wherein said high intensity light source is directed perpendicularly to a top surface of said color filter assembly.

11. The method of claim 1 wherein said high intensity light source is provided with a top hat energy profile.

12. The method of claim 1 further comprising the step of directing a high intensity light source through an aperture opening of selected size to remove a portion of said color filter disposed between said anomaly and said light source means.

13. The method of claim 12 wherein said high intensity light has energy of first and second wavelengths, said first wavelength energy for removing said portion of said color filter, and said second wavelength energy for ablating said anomaly.

14. The method of claim 13 wherein said light source means produces said first wavelength energy and said second wavelength energy simultaneously.

15. The method of claim 13 wherein said light source means produces said first wavelength energy then said second wavelength energy.

16. A method for repairing a color filter assembly for a flat panel display using a high intensity light source means, said color filter assembly having an anomaly, said color filter assembly having a plurality of color pixels being defined on a transparent substrate, said method comprising:

directing a high intensity light source through an aperture opening of selected size at said anomaly to a portion of said anomaly to ablate, eliminating said ablated portion of said anomaly; and adjusting said selected size of said aperture opening to direct said high intensity light source at a second portion of said anomaly to ablate.

17. A method of repairing a color filter assembly for a flat panel display, said method comprising steps of:

providing a color filter assembly, said color filter assembly having a plurality of color pixels, said color filter assembly having an anomaly, said anomaly being characterized by an upper surface protruding further out than surrounding regions;

directing a first high intensity light source through a first aperture at said anomaly to ablate a first portion of said anomaly, to eliminate said first portion of said anomaly; and directing a second high intensity light source through a second aperture at said anomaly to ablate a second portion of said anomaly, to eliminate said second portion of said anomaly.

18. The method of claim 17 wherein said first and second high intensity light sources are provided by a YAG laser.

19. The method of claim 17 wherein said anomaly is caused by a defect selected from a group of defects consisting of a particle, a photoresist, a pattern defect, a spike, or a bubble.

20. The method of claim 17 wherein said anomaly is defined in a portion of said filter selected from a group consisting of a protective layer, a matrix layer, and an electrode layer.

21. The method of claim 17 wherein said first portion of said anomaly has a greater surface area than said second portion of said anomaly.

22. The method of claim 17 further comprising steps of adjusting said aperture successively from said first aperture to said second aperture.

23. The method of claim 17 wherein said anomaly has a dimension of 10 micron and less.

24. The method of claim 17 wherein said each of directing steps has a positioning accuracy of 1 micron and less.

25. The method of claim 17 wherein each of said directing steps has a positioning accuracy of ½ micron and less.

26. The method of claim 17 wherein each of said directing steps is provided in about 2 seconds and less.

27. The method of claim 17 wherein said first and second high intensity light sources are substantially at a wavelength of about 350 nm to about 400 nm.

28. The method of claim 17 wherein said first and second high intensity light sources are directed perpendicularly to a top surface of said color filter assembly.

29. The method of claim 17 wherein said first and second high intensity light sources are provided with a top hat energy profile.

30. A method of repairing a color filter assembly for a flat panel display, said color filter assembly having an anomaly, said method comprising:

removing portions of said anomaly by repeatedly directing a high intensity light energy at said portions of said anomaly to ablate said portions; and wherein repeatedly directing said high intensity light is achieved by directing said high intensity light energy through an aperture having successively diminishing aperture size.

31. A method of repairing a color filter assembly for a flat panel display, said color filter assembly having an anomaly, said method comprising:

ablating portions of said anomaly by successively directing a high intensity light beam at said portions of said anomaly using successively diminishing light beam cross-section size; and wherein said successively diminishing light beam cross-section size is achieved by directing said high intensity light beam through an aperture having successively diminishing aperture size.

32. A method of repairing a color filter assembly for a flat panel display, said color filter assembly having an anomaly, said method comprising:

generating a high intensity light beam having a top hat beam cross-section profile shape wherein intensity of said high intensity light beam is substantially constant for a spatial dimension range; and directing said high intensity light beam through an aperture opening of selected size to a portion of said anomaly to ablate said portion of said anomaly;

wherein said directing further comprises successively directing said high intensity light beam at said anomaly using successively diminishing aperture size.

33. The method of claim 32 wherein said high intensity light beam is generated by a YAG laser having a wavelength no greater than 1.06 $\mu$m.

34. A method of repairing a color filter assembly for a flat panel display, said color filter assembly having an anomaly, said method comprising:

(a) directing a high intensity light through a selected aperture size at said anomaly to ablate the anomaly;

(b) inspecting said color filter to determine if said anomaly has been substantially removed; and (c) successively repeating steps (a) and (b) until said anomaly has been substantially removed from said color filter;

wherein step (c) uses successively diminishing aperture size.

* * * * *